(12) United States Patent
Peddicord et al.

(10) Patent No.: US 6,402,691 B1
(45) Date of Patent: Jun. 11, 2002

(54) IN-HOME PATIENT MONITORING SYSTEM

(76) Inventors: Herschel Q. Peddicord, 22133 Davidson Rd., Apt. 201, Waukesha, WI (US) 53186; Kent A. Tabor, 12704 N. River Rd., Mequon, WI (US) 53092

(*) Notice: Subject to any disclaimer, the term of this patent is extended or adjusted under 35 U.S.C. 154(b) by 0 days.

(21) Appl. No.: 09/665,768

(22) Filed: Sep. 20, 2000

Related U.S. Application Data

(60) Provisional application No. 60/155,012, filed on Sep. 21, 1999.

(51) Int. Cl.[7] .............................. A61B 5/00; H04B 7/00; H04M 1/24; H04M 3/08; H04Q 1/30
(52) U.S. Cl. ...................... 600/300; 600/301; 128/897; 128/903; 128/904; 455/39; 455/507; 455/899; 379/38; 379/106.02; 340/531; 340/799
(58) Field of Search ................................ 600/300–301, 600/481, 506, 508, 529, 532, 538, 544–545; 128/878, 897, 900, 903–904, 905; 705/2–3; 340/531–539, 825, 999; 379/37–38, 106.02; 455/421, 39, 507, 521, 524, 73–90, 91–92, 95, 899

(56) References Cited

U.S. PATENT DOCUMENTS

| | | |
|---|---|---|
| 4,259,548 A | 3/1981 | Fahey et al. |
| 4,838,275 A | 6/1989 | Lee |
| 5,270,770 A | 12/1993 | Kukimoto et al. |
| 5,339,821 A | 8/1994 | Fujimoto |
| 5,434,611 A | 7/1995 | Tamura |
| 5,438,607 A | 8/1995 | Przygoda et al. |
| 5,441,047 A | 8/1995 | David et al. |
| 5,454,024 A | 9/1995 | Lebowitz |
| 5,462,051 A | 10/1995 | Oka et al. |
| 5,488,412 A | 1/1996 | Majeti et al. |
| 5,502,726 A | 3/1996 | Fischer |
| 5,537,459 A | 7/1996 | Price et al. |
| 5,544,649 A | 8/1996 | David et al. |
| 5,544,661 A | 8/1996 | Davis et al. |

(List continued on next page.)

FOREIGN PATENT DOCUMENTS

| WO | WO 98/20439 | 5/1998 |
|---|---|---|

*Primary Examiner*—Kevin Shaver
*Assistant Examiner*—Michael Astorino
(74) *Attorney, Agent, or Firm*—Andrus, Sceales, Starke & Sawall, LLP

(57) ABSTRACT

A system for remotely monitoring the medical condition of a number of individual patients from a centralized location. The system includes a plurality of remote monitoring units that each include both a wireless transmission device and a conventional modem for communicating over voice telephone lines. The dual modes of transmission allow the remote monitoring unit to communicate either over a wireless communication network, if available or over conventional telephone wires. The remote monitoring unit includes a voice processing system that provides audio prompts and directions to the patient to direct the patient through the vital sign data gathering sequence. The audio prompts instruct the patient on the particular steps and timing for the vital sign data gathering sequence. Once the vital sign data has been acquired, the control unit of the remote monitoring unit determines whether a wireless transmission network is available. Based on the availability of the wireless communication network, the control unit of the remote monitoring unit selects either a wireless transmission or a conventional modem transmission method for the vital sign data. The vital sign data is compiled in a main data collection station that stores an displays the vital sign data for each patient being monitored. The vital sign data contained within the main data collection station is accessible by multiple workstations through conventional web-based communication techniques.

21 Claims, 8 Drawing Sheets

U.S. PATENT DOCUMENTS

| | | |
|---|---|---|
| 5,553,609 A | 9/1996 | Chen et al. |
| 5,558,638 A | 9/1996 | Evers et al. |
| 5,564,429 A | 10/1996 | Bornn et al. |
| 5,576,952 A | 11/1996 | Stutman |
| 5,594,638 A | 1/1997 | Iliff |
| 5,596,994 A | 1/1997 | Bro |
| 5,603,323 A | 2/1997 | Pflugrath et al. |
| 5,617,871 A | 4/1997 | Burrows |
| 5,619,991 A | 4/1997 | Sloane |
| 5,634,468 A * | 6/1997 | Platt et al. .................. 128/903 |
| 5,640,953 A | 6/1997 | Bishop et al. |
| 5,652,570 A | 7/1997 | Lepkofker |
| 5,666,487 A | 9/1997 | Goodman et al. |
| 5,678,562 A | 10/1997 | Sellers |
| 5,687,734 A | 11/1997 | Dempsey et al. |
| 5,712,619 A | 1/1998 | Simkin |
| 5,752,976 A | 5/1998 | Duffin et al. |
| 5,767,791 A | 6/1998 | Stoop et al. |
| 5,771,001 A | 6/1998 | Cobb |
| 5,810,747 A | 9/1998 | Brudny et al. |
| 5,987,519 A | 11/1999 | Peifer et al. |
| 6,050,940 A | 4/2000 | Braun et al. |
| 6,080,106 A * | 6/2000 | Lloyd et al. ................. 600/300 |
| 6,139,495 A * | 10/2000 | De La Huerga ............ 128/903 |
| 6,206,829 B1 * | 3/2001 | Iliff ............................ 600/300 |

\* cited by examiner

IN-HOME PATIENT MONITORING SYSTEM

CROSS-REFERENCE TO RELATED APPLICATIONS

This application is based on and claims priority from provisional patent application Ser. No. 60/155,012 filed on Sep. 21, 1999.

BACKGROUND AND SUMMARY OF THE INVENTION

The present invention generally relates to the remote monitoring of a patient. More specifically, the present invention relates to a monitoring system that can be installed in a patient's home and transmits select vital signs taken from the patient over a wireless communication network.

Congestive heart failure is a rapidly growing disease that affects an estimated 20 million people worldwide, including an estimated 4.7 to 6 million in the United States alone. According to the American Heart Association, more than 250,000 Americans die from congestive heart failure each year.

In the treatment of chronic illness, including congestive heart failure, diabetes, asthma and chronic obstructive pulmonary disease, it is important to monitor the patient on a regular basis since changes in the patient's vital signs, including weight, blood pressure, pulse rate and oxygen saturation, serve as indicators of the worsening of the patient's condition. Early detection of changes in these patient vital signs allow a physician to adjust the patient's medication, treatment or diet before the symptoms reach a critical state.

In order to constantly monitor a chronic disease patient, the patient must come into a clinic or hospital and have their vital signs monitored, sometimes on a daily basis. The cost to the clinic or hospital to perform the continuous monitoring of the patient is expensive and labor-intensive. As a consequence, patients are often monitored on a less frequent basis than is optimal.

Since many congestive heart failure patients are elderly and may not be able to transport themselves to a clinic or hospital, the process of returning to a clinic or hospital on a regular basis is a daunting prospect for many of these patients. Further, the congestive heart patients may live in remote rural locations, which requires the patient to make long commutes, which consumes a significant amount of the patient's time.

Therefore, a need exists for an in-home monitoring system that allows the patient to remain in his or her own home and collect the vital signs on a daily basis. Additionally, it is an object of the present invention to provide a remote monitoring unit that transmits the recorded vital signs to a remote main data collection station so that the collected data can be reviewed by a clinician. Further, it is an object of the present invention to store the collected patient vital signs in a database and trend the data over a selected time interval, such as daily/weekly/monthly. Further, it is an object of the present invention to provide a home monitoring system that is easy to use and utilizes audio instructions to direct the patient through the process of gathering their own vital signs. Further, it is an object of the present invention to provide a home monitoring system that transmits data over a wireless communication network. It is an additional object of the present invention to provide a home monitoring system that provides dual communication modes to ensure that the vital signs collected by the monitoring system of the present invention can be transmitted to the main data collection station, whether by wireless communication or standard telephone wiring.

Various other features, objects and advantages of the invention will be made apparent from the following description taken together with the drawings.

BRIEF DESCRIPTION OF THE DRAWINGS

The drawings illustrate the best mode presently contemplated of carrying out the invention.

In the drawings.

DETAILED DESCRIPTION OF THE INVENTION

Figure 1:
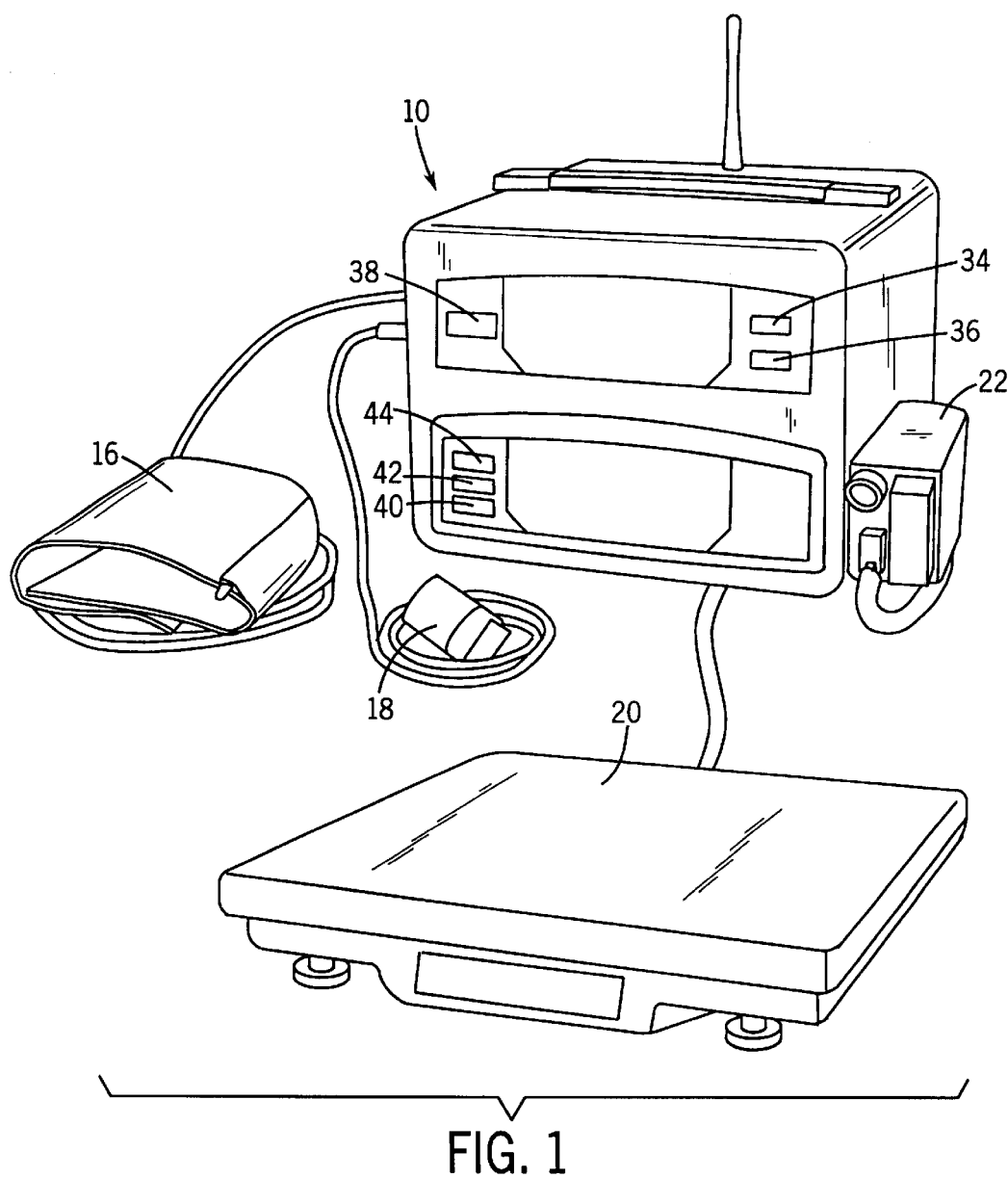
FIG. 1 is a perspective view illustrating an in-home remote monitoring unit for measuring and transmitting the vital signs of a patient that forms part of the monitoring system of the present invention.
Figure 3:
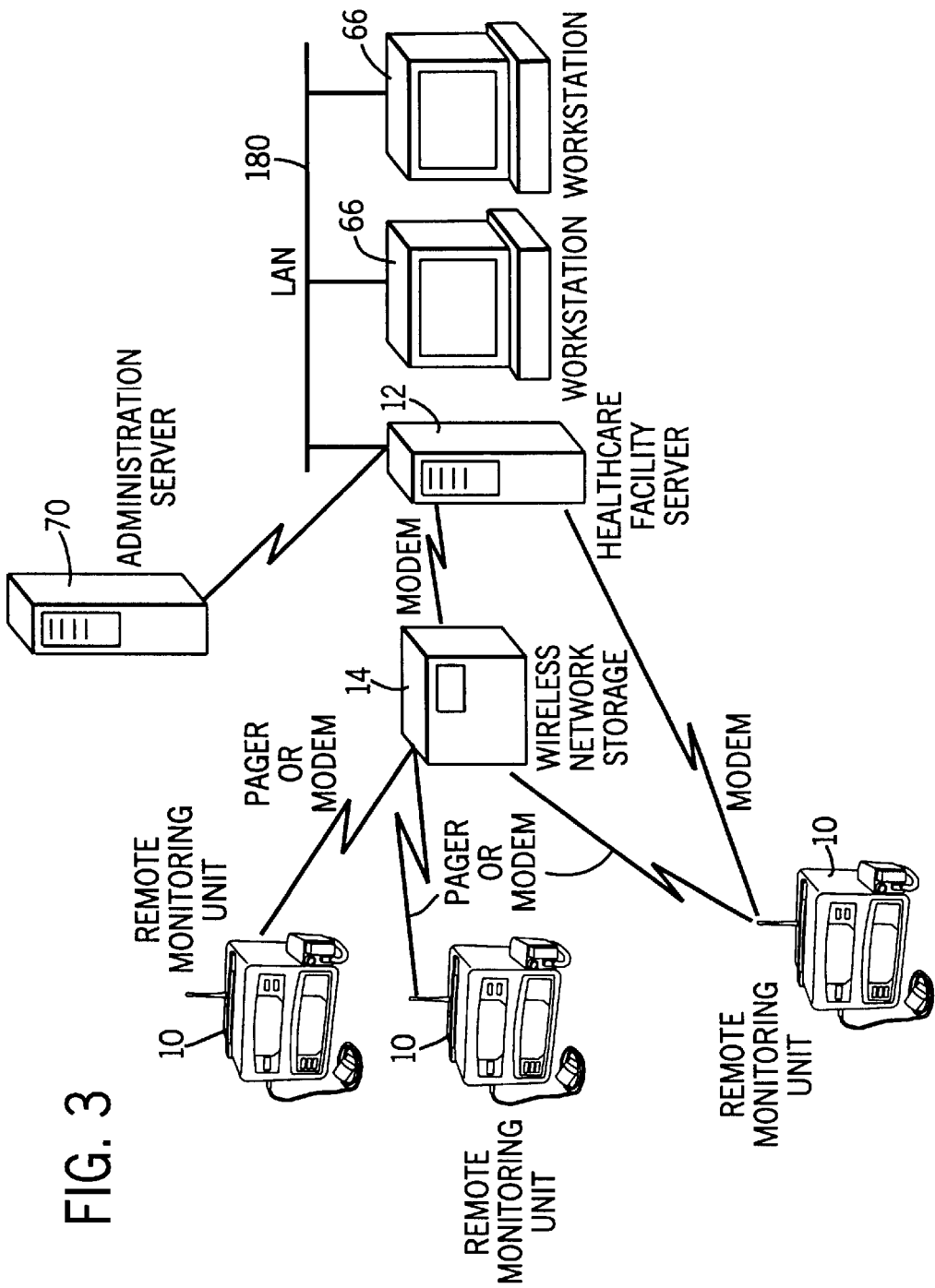
FIG. 3 is a schematic illustration of the monitoring system of the present invention showing the data transmission path from the in-home remote monitoring units to a health care facility responsible for patient monitoring.

Referring first to FIG. 1, thereshown is an in-home remote monitoring unit 10 for use in the medical monitoring system of the present invention. The monitoring unit 10 is a portable and transportable medical monitoring device that transmits measured patient vital signs to a main data collection station 12 through an intermediate wireless network storage unit 14, as best shown in FIG. 3. As can be seen in FIG. 3, multiple monitoring units 10 communicate either by a wireless communication device or conventional telephone modem with the wireless network storage unit 14, which in turn communicates with the main data collection station 12 such that the main data collection station 12 can simultaneously receive and monitor the vital signs of multiple patients.

Figure 2:
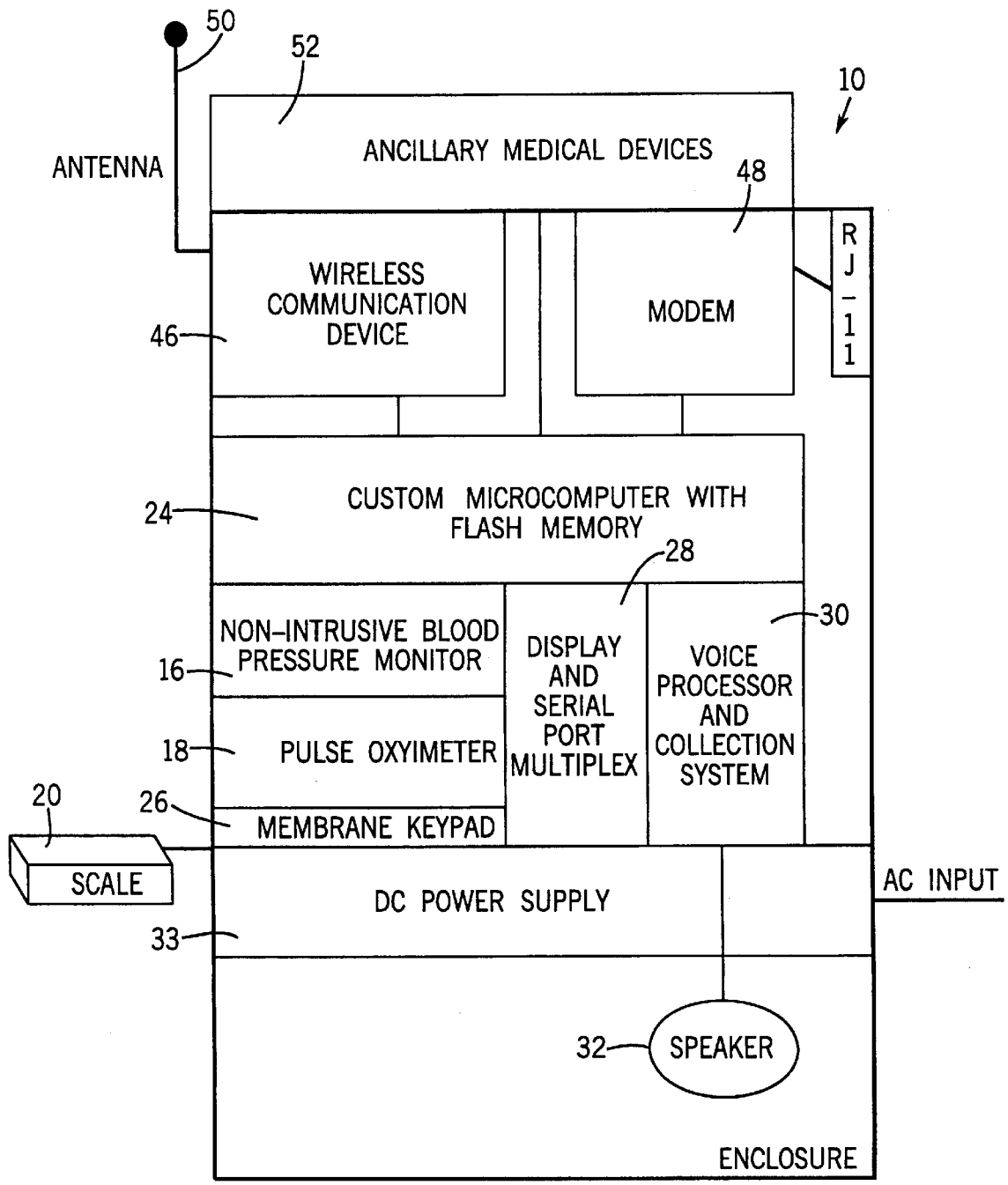
FIG. 2 is a schematic illustration of the internal components that are contained within the in-home remote monitoring unit shown in FIG. 1.

Referring now to FIGS. 1 and 2, the monitoring unit 10 of the present invention includes a plurality of external medical monitoring devices for measuring the vital signs of the patient using the monitoring unit 10. In the embodiment of the invention shown, each of the monitoring devices is hospital-grade such that the monitoring devices provide dependable and accurate measurements.

As shown in FIG. 1, the monitoring unit 10 includes a non-invasive blood pressure monitor (NIBP) 16, an pulse oximeter 18 and a scale 20. Additionally, the monitoring unit 10 shown in FIG. 1 includes an electronic thermometer 22. Each of the medical monitoring devices shown in FIG. 1 is commercially available and operates in a automated fashion such that the patient utilizing the monitoring unit 10 can easily record their own vital signs through the use of the monitoring unit 10. For example, in the preferred embodiment of the invention, the blood pressure monitor 16 is Model No. 6004, available from BCI International of Waukesha, Wis. The pulse oximeter 18 is Model No. 3304 also available from BCI International of Waukesha, Wis.

The digital scale 20 is Model No. TBF-310, available from Fairbank Scale Corporation. Although the specific examples of the monitoring devices listed above are used in the preferred embodiment of the invention, it is contemplated by the inventors that various equivalent components could be used while operating within the scope of the invention.

As can be seen in FIG. 2, the monitoring unit 10 includes a microcomputer control unit 24 that controls the operation of the monitoring unit 10. In the preferred embodiment, the control unit 24 is a 386 microprocessor with 2MB of flash memory. The control unit 24 is shown connected to the blood pressure monitor 16, the pulse oximeter 18 and the scale 20. Additionally, the control unit 24 is internally connected to a membrane keypad 26 that allows the patient to enter information into the control unit 24, a display 28 and a voice processor and collection system 30. The voice processor and collection system transmits audio messages through a speaker 32 to help guide the patient through the process of recording his/her vital signs by using the monitoring unit 10 of the present invention, as will be discussed in greater detail below. The monitoring unit 10 is powered by AC inputs which are coupled to internal AC/DC converters 33 that generate multiple DC voltage levels.

Referring back to FIG. 1, the membrane keypad illustrated in FIG. 2 includes several buttons contained on the face of the remote monitoring unit 10 that allow the patient to interact and respond to directions given to the patient by the remote monitoring unit 10. In the embodiment of the invention illustrated in FIG. 1, the face of the monitoring unit 10 includes a yes button 34, a no button 36, a repeat test button 38, an on/off button 40, a start blood pressure test button 42 and a stop blood pressure test button 44. These six buttons on the front face panel of the monitoring unit 10 allow the patient to respond to audio prompts generated by the monitoring unit 10 and control the process of obtaining their vital signs through the remote monitoring unit 10.

Referring back to FIG. 2, after the control unit 24 has collected the vital signs from the patient, the control unit 24 encodes the recorded vital signs and transmits the vital signs either through a wireless communication device, such as the wireless pager 46 or a conventional telephone modem 48. As can be seen in FIG. 2, the wireless pager 46 is connected to an antenna 50 to transmit the encoded vital signs to the wireless network storage unit 14, as shown in FIG. 3.

During the initial installation of the monitoring unit 10, the conventional telephone modem 48 is connected to a telephone outlet by a conventional telephone cord. The conventional modem 48 connection serves as a back-up and is used when the wireless method of communication is unavailable for any number of reasons. For example, the patient and the monitoring unit 10 may be located in a remote area where wireless service is not present, such that the monitoring unit 10 would then rely on the conventional modem 48.

Each time the control unit 24 plans to transmit vital signs to the main data collection station 12, the control unit 24 checks to make sure that a wireless communication link is available to the wireless network storage unit 14. If the wireless communication link 14 is available, the control unit 24 transmits the encoded vital signs through the wireless communication device 46. However, if the wireless communication link 14 is not available for any reason, the control unit 24 transmits the vital signs through the conventional modem 48. In this manner, the monitoring unit 10 of the present invention can be used in almost any location since the monitoring unit 10 does not require that a wireless communication connection be available.

As can be seen in FIG. 2, an ancillary medical device 52 can be coupled to an auxiliary input of the monitoring unit 10. It is contemplated by the inventors that various ancillary medical devices, such as an automated glucose monitoring meter for monitoring diabetes or a spirometer for monitoring an asthma patient are contemplated as being useful additions to the monitoring unit 10. Additionally, it is contemplated that an automated card reader could be connected to the auxiliary input to allow a single monitoring unit to be used by multiple patients. For example, the monitoring unit could be located in a clinic and each patient of the clinic would have a patient identification card including a distinct patient identifier. In addition, the ID card can also contain patient specific configuration parameters, such as the initial inflation pressure of the blood pressure cuff. The card reader would scan the patient ID card and transmit the patient ID number with the vital sign data packet such that the main data collection station could identify the patient.

Figure 4:
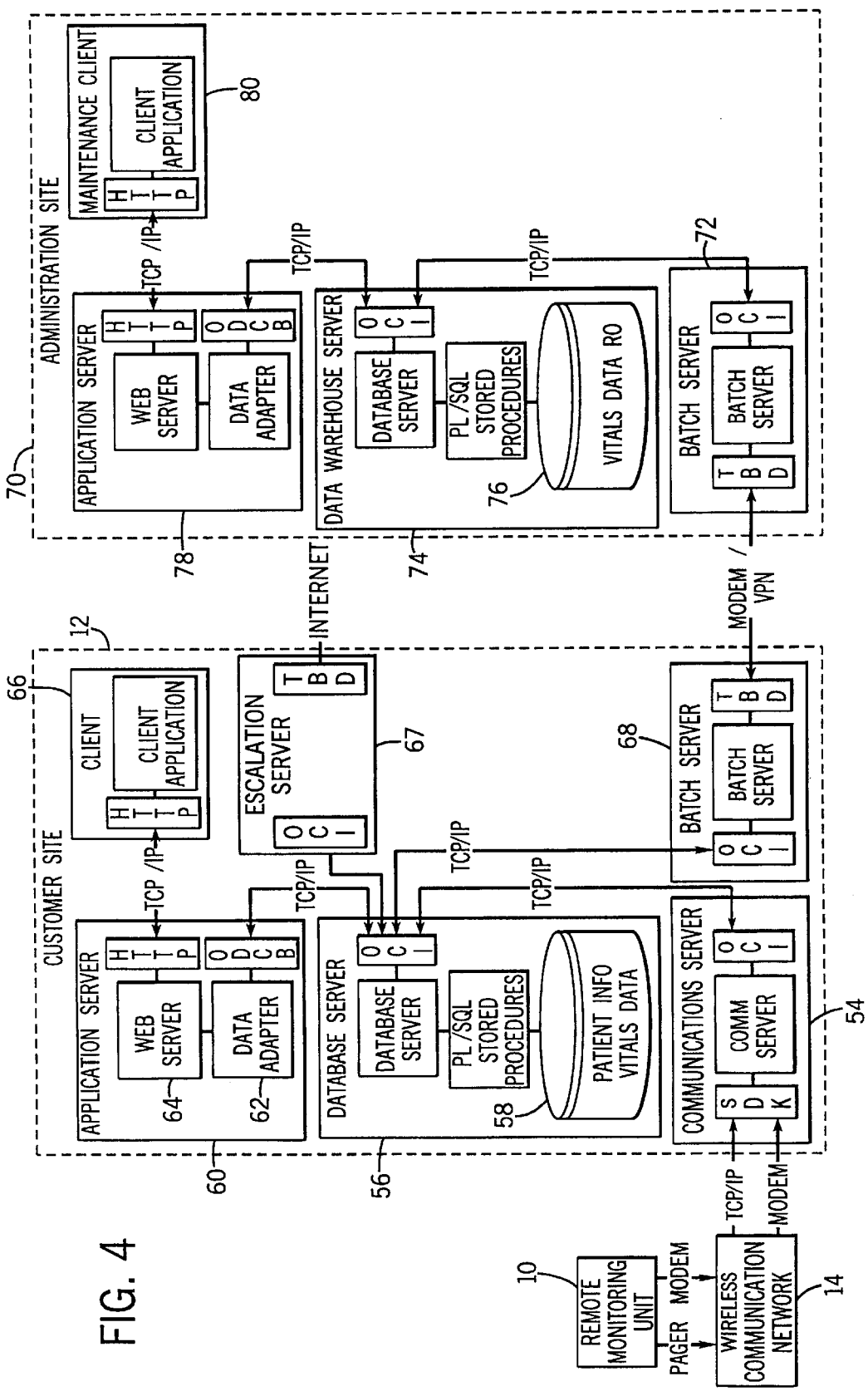
FIG. 4 is a schematic illustration of the system architecture for the main data collection station that receives the transmitted vital signs from the remote monitoring units.

Referring now to FIG. 4, thereshown is the internal structure of the main data collection station 12 that receives the vital sign data sent from the remote monitoring unit 10. As discussed previously, the vital sign data is transmitted by the remote monitoring unit 10 by either a wireless communication device or conventional modem to the wireless network storage unit 14. After receiving the vital sign data, the wireless network storage unit 14 can be accessed by the main data collection station 12 through either a conventional modem connection or a TCP/IP communication link. As discussed previously, the main data collection station 12 is typically located in a health care facility, such as a clinic or hospital, that monitors the vital signs of numerous patients from a centralized location. The main data collection station 12 allows health care personnel to monitor the vital signs of numerous patients from a centralized location without requiring the patient or a health care worker to physically interact with each other.

The main data collection station 12 includes a communications server 54 that communicates with the wireless network storage unit 14. The wireless network storage unit 14 is a centralized computer server that includes a unique, password protected mailbox assigned to and accessible by the main data collection station 12. In the preferred embodiment of the invention, the wireless network storage unit 14 is provided by Skytel and stores the received vital sign data for up to 72 hours. The main data collection station 12 contacts the wireless network storage unit 14 by either TCP/IP or a conventional telephone modem and downloads the vital sign data stored in the mailbox assigned to the main data collection station 12.

Once the communications server 54 has formed a link with the wireless network storage unit 14 and downloaded the patient vital sign data, the patient data is transferred to a database server 56. The database server 56 includes a patient database 58 that records and stores the vital signs of the patients based upon identification included in the data packets sent by each of the remote monitoring units 10. For example, each data packet includes an identifier that allows the database server 56 to determine which remote monitoring unit 10 the information was taken from.

Each data packet transferred from the remote monitoring unit 10 to the main data collection station does not include any patient identifiable information. Instead, the data packet includes the serial number assigned to the specific remote monitoring unit 10. The serial number associated with the monitoring unit 10 can then be correlated to a specific patient by using information stored on the patient database 56. In this manner, the data packets transferred through the wireless network storage unit 14 do not include any patient-specific identification. Therefore, if the data packets are intercepted or improperly routed, patient confidentiality is not breached.

The database server 56 is accessible by an application server 60. The application server 60 includes a data adapter 62 that formats the vital sign information into a form that can be viewed over a conventional web-based connection. The transformed data from the data adapter 62 is accessible by propriety application software through a web server-64 such that the data can be viewed by a client workstation 66. The client workstation 66 is a conventional personal computer that can access the patient data using proprietary software applications through HTTP protocol.

The main data collection station further includes an escalation server 67 that communicates with the database server 56. The escalation server monitors the vital sign data packets that are received by the database server 56 from the remote monitoring units. Specifically, the escalation server periodically polls the database server for unacknowledged vital sign data packets. If the data packets are not acknowledged by medical personnel within a pre-determined time period, the escalation server 67 automatically generates a notification message to a selected clinician. For example, the escalation server can be programmed to automatically deliver a pager message/email/fax to a specific clinician if an alarm message has not been acknowledged within a selected time period after receipt of the data packet. The escalation server 67 can be configured by the health care facility to generate the notification message to different people by different modes of communication after different delay periods and during different time periods depending upon the specific wishes of the facility. The notification message allows the health care facility to make sure that vital sign data packets are acknowledged in a timely manner. For example, if the main data collection station is not staffed in the evenings, the collection station can be programmed such that from 6 pm to 6 am Monday through Friday, if any medical alerts are not acknowledged within thirty minutes, a specified clinician is paged.

The main data collection station 12 includes a batch server 68 connected to the database server 56. The batch server 68 allows an administration server 70, as shown in FIGS. 3 and 4, to have access to the vital sign data stored in the patient database 58. The administration server allows for centralized management of medication information and patient diagnosis classifications.

The administration server 70 includes a batch server 72 that communicates with the batch server 68 and provides the downloaded data to a data warehouse server 74. The data warehouse server 74 includes a large database 76 that records and stores the patient vital sign data.

The administration server 70 further includes an application server 78 and a maintenance workstation 80 that allow personnel from the administrator to access and monitor the data stored in the database 76.

Referring now to FIGS. 5a–5f, the automated operating steps performed by the remote monitoring unit 10 will now be described. Initially, when the monitoring unit 10 is installed in the patient's home, the monitoring unit is plugged into an AC outlet and the conventional modem 48 is connected to a telephone outlet. Once the monitoring unit 10 is properly connected, the monitoring unit 10 is turned on and the control unit begins its internal program, as illustrated in step 82. The first step in the program is to determine whether the time for the vital signs to be recorded for the patient has been reached, as indicated in step 84. If the time has not yet been reached, the control unit displays the present time in step 86 and continues the loop as shown. The time at which the vital signs are to be recorded is programmed into the remote monitoring unit by the health care provider and is typically selected as a convenient time for the patient to be at home and capable of performing the vital sign measurements required.

Once the time for the vital signs to be recorded is reached or the repeat test button 38 has been depressed, the control unit generates an audio message to the patient letting the patient know that it is now time for the vital signs to be recorded, as illustrated in step 88. In the embodiment of the invention illustrated, the monitoring unit 10 wishes the patient a good morning and tells the patient that it is now time for the patient to record his or her vital signs.

After the patient has been told that the time has been reached to record the vital signs, the patient is given an audio prompt to step on the digital scale. After the audio prompt has been given to the patient to step on the scale, the control unit monitors to determine whether a valid reading has been generated by the digital scale within a selected time period, such as one minute, as illustrated in step 92. If a valid reading has been generated within the one minute time period, the control unit displays the recorded weight on the display for the monitoring unit.

However, if the scale fails to generate a valid weight reading within the one minute time period, the control unit again generates an audio prompt to the patient to step on the scale, as indicated in step 96. The control unit again determines whether or not a valid reading has been taken in an extended time period, such as fourteen minutes as illustrated in step 98. If a valid reading is not recorded within this expanded time, the control unit again prompts the patient to step on the scale, as illustrated in step 100. Once again, if a valid weight has not been recorded, as monitored in step 102, the control unit ends the attempt to record the weight, as illustrated in step 104. If no valid weight has been recorded, the control unit puts null data into the vital sign data packet and continues on to the transmission section of the process, as will be discussed in detail below.

The data packet utilized in the transmission of the vital sign data is a variable length ASCII character packet in which the various vital sign measurements are placed in a specific sequence with the specific readings separated by commas. The control unit of the remote monitoring unit converts the readings from each of the medical devices into a standardized sequence that forms part of the vital sign data packet. In this manner, the control unit can be programmed to convert the vital sign readings from various types of medical monitoring devices into a standardized data packet that can be interpreted and displayed by the main data collection station.

If the digital scale fails to generate a valid reading, as illustrated in step 104, the control unit fills the portion of the vital sign data packet associated with the scale with a null indicator. In the preferred embodiment of the invention, the null indicator is the lack of any characters between commas in the vital sign data packet. The lack of characters in the data packet indicates that the patient was not available for the vital sign recording. The null indicator in the vital sign data packet is interpreted by the main data collection station 12 as a failed attempt to record the vital signs due to the unavailability of the patient or a malfunction in one of the medical devices. The null indicator received by the main data collection station 12 indicates that the transmission from the remote monitoring unit was successful, even though the patient was unable to successfully record his or her vital signs. In the preferred embodiment of the invention, the integrity of the data packet received by the main data collection station is determined using a cyclic redundancy code, CRC-16, check sum algorithm. The check sum algorithm is applied to the data when the message is sent and then again to the received message.

If the digital scale recorded a valid weight reading, the control unit puts the weight data in the vital sign data packet, as illustrated in step 106. As discussed previously, the vital sign data packet will include all of the vital signs recorded by the remote monitoring unit.

After the weight data has been placed in the vital sign data packet, the control unit generates an audio prompt that tells the patient to step off the digital scale and sit down in a comfortable location, as illustrated in step 108.

Figure 5A:
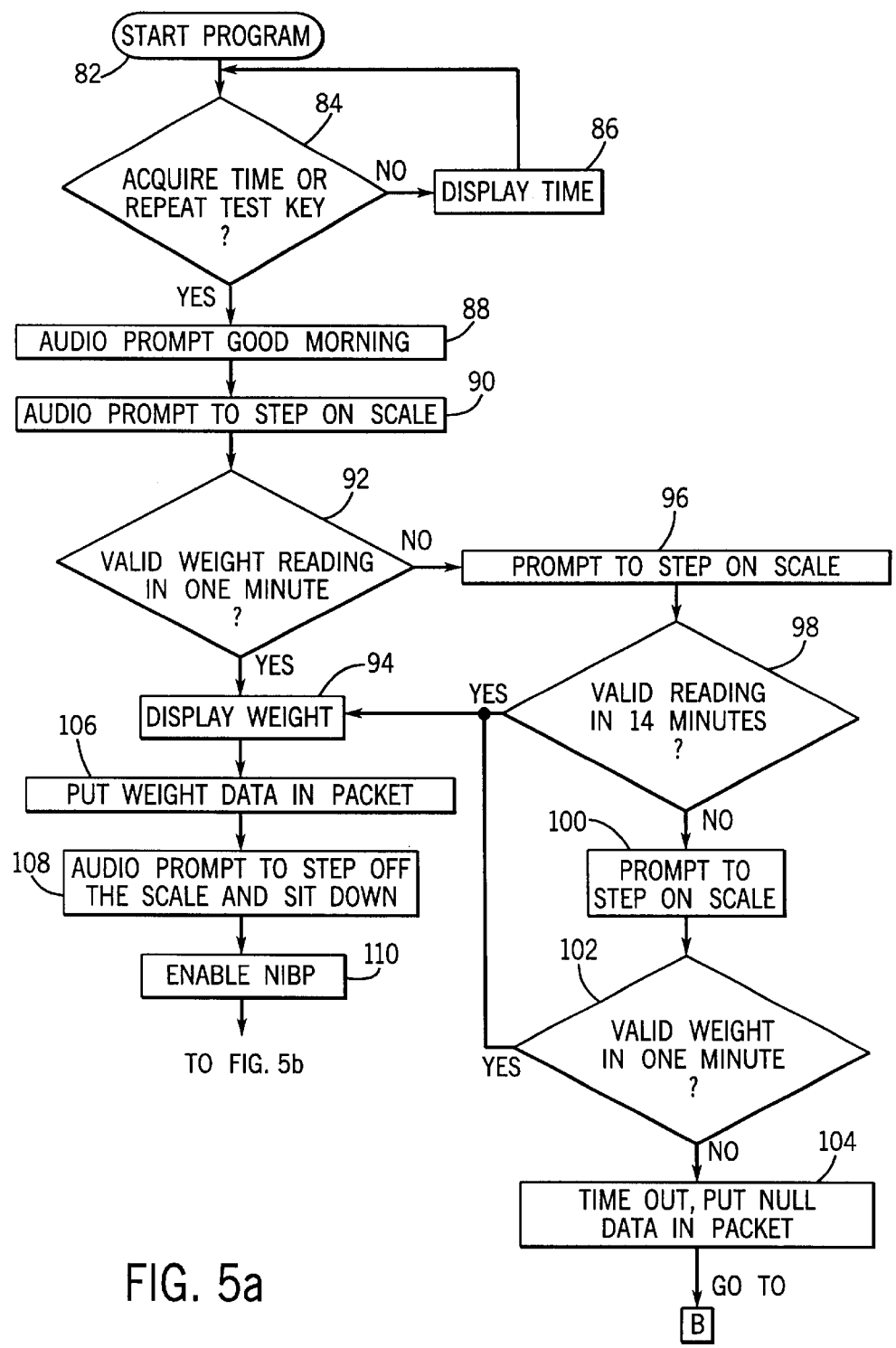
FIGS. 5a–5d are operational flowcharts illustrating the operational steps performed by the in-home remote monitoring unit of the present invention in recording and transmitting the vital signs to the main data collection station.
Figure 5B:
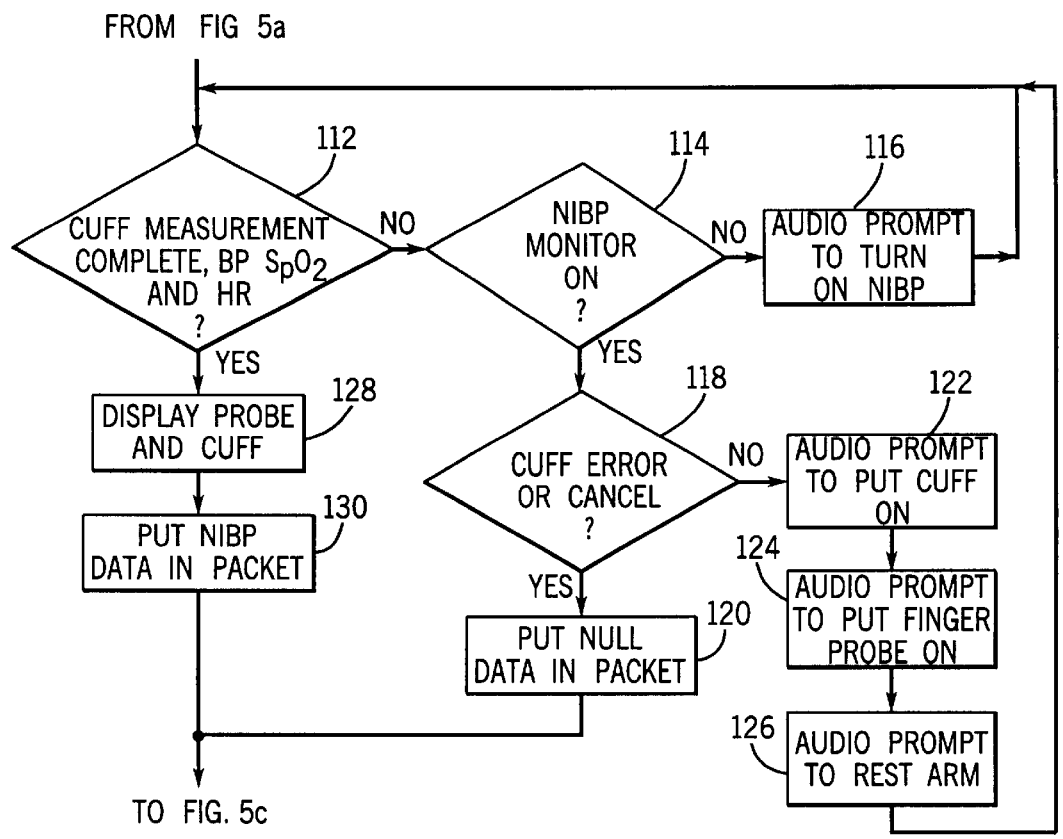
Figure 5C:
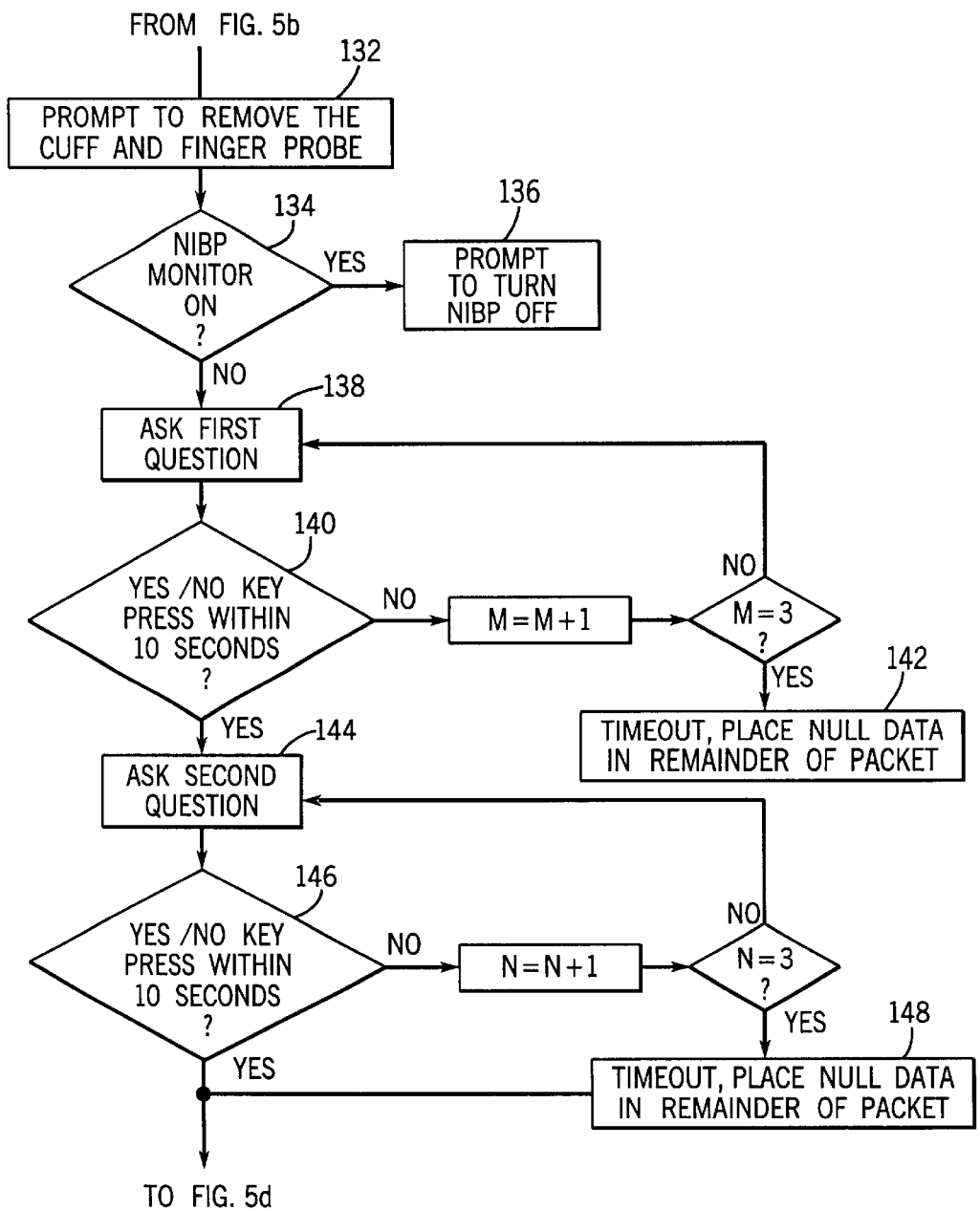
Figure 5D:
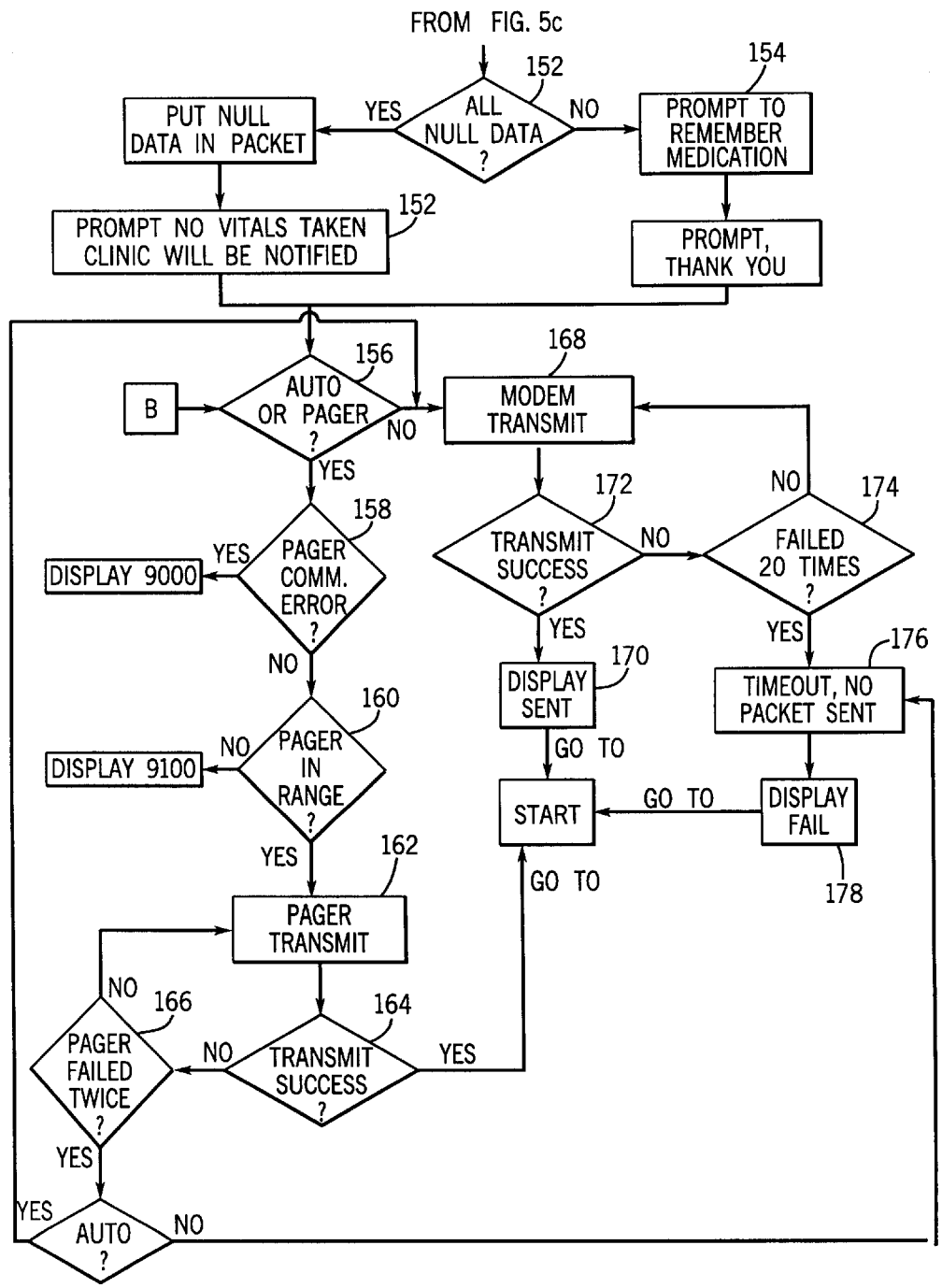

After the audio prompt has been generated, the control unit enables the non-invasive blood pressure monitor (NIBP) as illustrated in step 110 and the control unit begins the blood pressure measurement sequence, as illustrated in FIG. 5b.

Referring now to FIG. 5b, the control unit initially determines whether the cuff measurement has been complete and the blood pressure, $SpO_2$ and heart rate have been determined, as illustrated in step 112. If the blood pressure measurements have not yet been taken, the control unit determines whether the blood pressure monitor has been turned on, as indicated in step 114. If the blood pressure monitor has not yet been turned on, the control unit generates an audio prompt requesting the patient to turn on the blood pressure monitor, as illustrated in step 116. To turn on the blood pressure monitor, the user depresses the on/off switch 40, as illustrated in FIG. 1

Once the blood pressure monitor has been turned on, the control unit determines whether or not the blood pressure cuff is operating properly, as illustrated in step 118. If the blood pressure cuff is operating improperly, the control unit puts null data in the vital sign data packet and proceeds onto the next monitoring step.

If the blood pressure cuff is operating properly, the control unit generates an audio prompt asking the patient to put the blood pressure cuff on and tighten the blood pressure cuff securely, as illustrated by step 122. Once the blood pressure cuff has been placed over the patient's arm, the control unit generates another audio prompt requesting the patient to put the finger sensor on the middle finger of their left hand, as illustrated by step 124. Once the blood pressure cuff and finger sensor have been placed on the patient, the patient is prompted to rest their arm comfortably in their lap, as illustrated by step 126. After the three audio messages 122, 124 and 126 have been generated, the control unit operates the blood pressure monitor and finger sensor to record the blood pressure, heart rate and $SpO_2$ concentration for the patient.

Any time during the NIBP vital sign acquisition process, the patient can use the electronic thermometer 22 to record his or her temperature. The control unit of the remote monitoring unit places the temperature into the vital sign data packet as appropriate.

After the vital sign measurements are complete, the control unit displays the sensor data and blood pressure cuff data as illustrated by step 128. In addition to displaying this data, the vital sign data is placed in the vital sign data packet, as illustrated in step 130. At this time, the vital sign data packet includes both the blood pressure and finger sensor measurements, as well as the weight of the patient from the digital scale.

Although not shown in the present invention, the remote monitoring unit can also take additional measurements utilizing one or more auxiliary devices such as those mentioned previously. Since the vital sign data packet has a variable length, the auxiliary device vital sign information would then be added to the vital sign data packet being compiled by the remote monitoring unit during the vital sign acquisition period being described.

After the control unit has acquired the vital sign information, the control unit generates an audio prompt telling the patient to remove the blood pressure cuff and finger sensor, as illustrated in step 132. After the blood pressure cuff and finger sensor have been removed, the control unit determines whether the blood pressure monitor is still on, as shown in step 134. If the blood pressure monitor is still on, the monitoring unit generates an audio prompt asking the user to depress the on/off button 40 to turn the blood pressure monitor off, as illustrated in step 136.

Once the blood pressure monitor has been turned off, the monitoring unit asks the patient a first question, as illustrated in step 138. For example, the first question may ask the patient if they were experiencing more difficulty breathing today as compared to a normal day. Based upon this question, the user depresses one of the yes and no keys 34 and 36. This answer is then added to the vital sign data packet.

After the first question has been asked, the control unit monitors to determine whether the yes/no keys 34 and 36 have been pressed within ten seconds, as shown in step 140. If the keys have not been depressed, an internal flag is increased. If the internal flag is less than three, the control unit re-asks the first question and monitors whether the key has been depressed. If more than three iterations have gone by, the control unit places a null indicator in the vital sign data packet, as illustrated in 142. The null indicator indicates that the patient has failed to respond to one of the questions asked by the monitoring unit.

After the first question has been asked, the monitoring unit asks a second question, as illustrated in step 144. For example, the second question may ask the patient whether or not they are more fatigued today as compared to a normal day. Upon hearing the questions, the patient responds by again depressing one of the two yes and no keys 34 and 36. The answer to this question is also placed in the vital sign data packet.

The control unit again monitors to determine whether the second question has been answered, as illustrated in step 146. The control unit again monitors to determine whether the answer has been entered within a predetermined time period. If the answer has not been given in the time period, the control unit again asks the second questions and waits for a response. After three iterations of this process, the control unit places a null indicator in the vital sign data packet, as illustrated by step 148. Again, the null indicator indicates that the patient has failed to respond to the question being asked by the remote monitoring unit.

After the questions have been answered, the control unit determines whether the vital sign data packet includes all null data, as illustrated in step 150. If the data packet does indeed include all null data, this indicates that the patient has been unable to record acceptable vital sign information and the control unit generates an audio prompt indicating that no vital signs have been taken and that the clinic will be notified, as illustrated in step 152.

If the vital sign data packet does not include all null data, the vital signs have been successfully recorded and the control unit generates an audio prompt reminding the patient to take his or her medication, as illustrated by step 154. After the patient has been reminded to take their medication, the control unit determines whether the monitoring unit has been set to either transmit using only the wireless communication device, only the conventional modem or set in the automatic mode, as illustrated in step 156. In the automatic mode, the monitoring unit first tries the wireless method of communication, and if the wireless method is not available, tries the conventional modem. These three settings for the transmission method allows the remote monitoring unit to save time if it is known that either the wireless network is not available or if a telephone line is not available If the remote monitoring unit is set in either the auto mode or the wireless only mode, the monitoring unit first determines if there is an internal pager communication error, as illustrated in step 158.

If no pager communication error is noted, the control unit determines whether the wireless pager is in range of a transmission station, as illustrated in step 160. If the pager is either out of range or a communication error is noted, the control unit proceeds to the conventional modem transmission sequence, as will be described below. However, if the wireless pager is working and in range of a communication tower, the control unit transmits the vital sign information over the wireless network, as illustrated in step 162. After the pager has transmitted the data packet, the control unit determines whether the transmission was successful, as illustrated in step 164. If the transmission has been unsuccessful only once, the control unit retries the transmission. However, if the wireless pager has failed twice, as illustrated in step 166, the control unit proceeds to the conventional modem process if the remote monitoring unit was configured in the auto mode.

In the conventional modem process, the control unit transmits the vital sign data over the conventional telephone connection by the conventional modem in the control unit, as illustrated in step 168. If the transmission has been successful, the display of the monitoring unit displays a successful message, as illustrated in step 170. However, if the control unit determines in step 172 that the conventional modem has failed to transmit the vital sign data over the conventional telephone wires, the control unit repeats the transmission until the control unit either successfully completes the transmission or determines that the transmission has failed twenty times, as illustrated in step 174. If the conventional modem has failed to transmit the information for twenty attempts, the control unit times out and failure message is displayed, as illustrated in steps 176 and 178. Once the transmission sequence has either failed or successfully transmitted the data to the main data collection station, the control unit returns to the start program step 82 as illustrated in FIG. 5a.

As discussed previously, the vital sign data packets are first sent and stored in the wireless network storage unit 14. From there, the vital sign data packets are downloaded into the main data collection station 12. The main data collection station 12 decodes the encoded vital sign data packets and records the vital signs in the patient database 58. The patient database 58 is divided into individual storage locations for each patient such that the main data collection station 12 can store and compile vital sign information from a plurality of individual patients.

As can be seen in FIG. 3, the patient database 58 is accessible by clinicians workstations 66 through a healthcare facility LAN 180. Unauthorized access to the patient database is prevented by individual clinician usernames and passwords to provide additional security for the patient's recorded vital sign data.

The main data collection station 12 and the series of work stations 66 allow health care personnel to monitor the daily vital sign measurements taken by the plurality of patients reporting vital sign data to the single main data collection station 12. The main data collection station is configured to display multiple patients on the display of the workstations 66 such that medical personnel can monitor a number of patients at a time. The internal programming for the main data collection station 12 operates such that the patients are placed in a sequential top-to-bottom order based upon whether or not the patient is generating an alarm signal for one of the vital signs being monitored. For example, if one of the patients being monitored has a blood pressure exceeding a predetermined maximum amount, this patient will be moved toward the top of the list of patients and the patient's name and/or vital sign data is highlighted such that the medical personnel can quickly identify those patients who may be in need of medical assistance. Listed below is a representative order ranking method for determining the order which the patients being monitored are displayed:

Alarm Display

| Order | Patient Status | Patients are then sorted |
| --- | --- | --- |
| 1 | Medical Alarm | Most alarms violated to least alarms violated, then oldest to newest |
| 2 | Missing Data Alarm | Oldest to newest |
| 3 | Late | Oldest to newest |
| 4 | Reviewed Medical Alarms | Oldest to newest |
| 5 | Reviewed Missing Data Alarms | Oldest to newest |
| 6 | Reviewed Null | Oldest to newest |
| 7 | NDR | Oldest to newest |
| 8 | Reviewed NDR | Oldest to newest |

Stable Display

| Order | Patient Status | Patients are then sorted |
| --- | --- | --- |
| 1 | Stable | Oldest to newest |
| 2 | No Set Alarms No Alarm Conditions | Alphabetically |

As listed in the table above, the order of patients listed on the display is ranked based upon the seriousness and number of alarms that are registered based upon the latest vital sign information. For example, if the blood pressure of a single patient exceeds the tolerance level and the patient's heart rate also exceeds the maximum level, this patient will be placed above a patient who only has one alarm condition. In this manner, the medical care personnel can quickly determine which patient most urgently needs medical attention by simply identifying the patient's name at the top of the patient list. The order which the patients are displayed is configurable by the healthcare facility depending on the preferences of the facility.

As discussed previously, the escalation server 67 automatically generates a notification message to a specified clinician for unacknowledged data packets based on user specified parameters.

In addition to displaying the current vital sign data for the numerous patients being monitored, the software of the main data collection station 12 allows the medical care personnel to trend the vital sign data over a number of prior measurements in order to monitor the progress of a particular patient. In addition, the software allows the medical care personnel to determine whether or not a patient has been successful in recording their vital signs as well as monitor the questions being asked by the remote monitoring unit. In addition, it is contemplated by the inventors that various other features could be added to the main data collection station to tailor the patient monitoring.

Various alternatives and embodiments are contemplated as being within the scope of the following claims particularly pointing out and distinctly claiming the subject matter regarded as the invention.

We claim:

1. A system for remotely monitoring the medical condition of a plurality of patients, the system comprising:
   a plurality of remote monitoring units each operable to measure selected vital signs from a patient, each monitoring unit including both a wireless transmission device for transmitting the measured vital signs over a wireless communication network and a back-up modem for transmitting the measured vital signs over conventional telephone wires; and
   a main data collection system configured to receive the vital signs transmitted by the plurality of remote monitoring units, wherein the main data collection system stores the received vital signs from the plurality of patients,
   wherein each of the remote monitoring units includes a control unit that transmits the measured vital signs by the wireless transmission device when the wireless communication network is available and transmits the measured vital signs by the back-up modem only when the wireless communication network is unavailable.

2. The system of claim 1 wherein each of the remote monitoring units further comprises:
   a digital scale coupled to the control unit for measuring the weight of the patient;
   a blood pressure monitor coupled to the control unit for measuring the blood pressure of the patient; and
   a pulse oximeter coupled to the control unit for measuring the heart rate and oxygen saturation of the patient.

3. The system of claim 2 wherein the each remote monitoring unit further includes at least one auxiliary input coupled to the control unit, the auxiliary input being configured to receive an auxiliary medical monitoring device.

4. The system of claim 3 wherein the auxiliary medical device is an ID card reader coupled one of the auxiliary inputs, the ID card configured to read an ID card assigned to each patient such that the monitoring unit can identify the patient.

5. The system of claim 2 wherein the control unit compiles the weight of the patient, the blood pressure of the patient, the heart rate and oxygen saturation of the patient into a single vital sign data packet which represents the measured vital signs for the patient.

6. The system of claim 5 wherein the control unit encodes the vital sign data packet prior to transmission of the data packet by the control unit.

7. The system of claim 1 wherein each monitoring unit further includes a voice processor and speaker coupled to the control unit such that the control unit can generate audio messages to the patient through the voice processor and speaker.

8. The system of claim 7 wherein the audio messages created by the control unit are audio prompts directing the patient to record their vital signs.

9. The system of claim 1 wherein the wireless transmission device is a wireless transceiver.

10. A system for remotely monitoring the medical condition of a patient, the system comprising:
    a plurality of monitoring units each being operable to measure selected vital signs from a patient, each monitoring unit including a wireless transmission device for transmitting the measured vital signs over a wireless communication network and a back-up modem for transmitting the measured vital signs over conventional telephone wires, each monitoring unit further including a control unit coupled to a voice processor and a speaker, wherein the control unit generates audible message to provide instructions to the patient through the voice processor and the speaker;
    a network storage unit operable to receive and store the measured vital signs transmitted by the monitoring units, the network storage unit having a separate mailbox assigned to store the transmitted measured vital signs from the plurality of monitoring units; and
    a main data collection system configured to access the network storage unit to download the vital signs transmitted by the monitoring units and stored in the network storage unit, wherein the main data collection system stores the downloaded vital signs for the plurality of patients,
    wherein the control unit transmits the measured vital signs by the wireless transmission device when the wireless communication network is available and transmits the measured vital signs by the back-up modem only when the wireless communication network is unavailable.

11. The system of claim 10 wherein each of the monitoring units further comprises:
    a digital scale coupled to the control unit for measuring and transmitting the weight of the patient to the control unit;
    a blood pressure monitor coupled to the control unit for measuring and transmitting the blood pressure of the patient to the control unit; and
    a pulse oximeter coupled to the control unit for measuring and transmitting the heart rate and oxygen saturation of the patient to the control unit;
    wherein the control unit generates the audible message to direct the patient through the steps required to measure the weight, blood pressure, heart rate and oxygen saturation from the patient.

12. A method of monitoring the vital signs of a plurality of patients from a central location, the method comprising the steps of:
    positioning a monitoring unit at a remote location with each patient, the monitoring unit including a wireless communication device for transmitting the vital signs over a wireless communication network and a back-up modem for transmitting the measured vital signs of the patient over conventional telephone wires;
    operating the monitoring unit to measure the vital signs of the patient at predetermined time intervals;
    determining the availability of the wireless communication network;
    transmitting the measured vital signs with the wireless communication device when the wireless communication network is available;
    transmitting the measured vital signs with the back-up modem over the conventional telephone wires only when the wireless communication network is unavailable, and receiving and storing the vital signs in a main data collection unit at the central location for each of the patients.

13. The method of claim 12 wherein the steps of measuring the vital signs of the patient include:

measuring the weight of the patient;

measuring the blood pressure of the patient; and measuring the pulse rate and blood oxidation of the patient.

14. The method of claim 13 further comprising the step of operating the monitoring unit to generate audio messages to the patient to direct the patient through the steps of measuring the vital signs of the patient.

15. The method of claim 13 further comprising the step of measuring the temperature of the patient.

16. The method of claim 12 wherein the vital signs of the patient are measured once each day.

17. The method of claim 12 wherein the vital signs of the patient are measured up to four times each day.

18. The method of claim 12 further comprising the step of:

receiving and storing the transmitted vital signs in a network storage unit, the network storage unit having a mailbox assigned to the main data collection unit; and operating the main data collection unit to download the stored vital signs from the network storage unit.

19. The method of claim 18 wherein the vital signs downloaded from the network storage unit include a serial number assigned to each patient being monitored such that patient identifiable information is not stored in the network storage unit.

20. The method of claim 12 further comprising the steps of:

generating a prioritized patient list at the main data collection unit based upon the vital signs downloaded, the patient list being prioritized based on the immediate need for medical attention;

requesting a medical personnel to acknowledge the vital signs for each member of the prioritized patient list within a selected time period after downloading of the vital signs; and generating a notification message to the medical personnel when the vital signs are not acknowledged in the time period.

21. The method of claim 20 wherein the notification message is a wireless page to the medical personnel.

\* \* \* \* \*